United States Patent [19]
Prutchi

[11] Patent Number: 5,531,772
[45] Date of Patent: Jul. 2, 1996

[54] RATE RESPONSIVE CARDIAC PACEMAKER WITH FILTERED IMPEDANCE SENSING AND METHOD

[75] Inventor: David Prutchi, Lake Jackson, Tex.

[73] Assignee: Intermedics, Inc., Angleton, Tex.

[21] Appl. No.: 342,436

[22] Filed: Nov. 18, 1994

[51] Int. Cl.$^6$ .................................................. A61N 1/365
[52] U.S. Cl. ............................................................. 607/17
[58] Field of Search .................................. 607/18, 19, 20, 607/21, 22, 23, 24, 17; 128/734

[56] References Cited

U.S. PATENT DOCUMENTS

| | | |
|---|---|---|
| 4,686,897 | 8/1987 | Salo et al. . |
| 4,901,725 | 2/1990 | Nappholz et al. . |
| 5,137,019 | 8/1992 | Pederson et al. ..................... 607/20 |
| 5,154,171 | 10/1992 | Chirife . |
| 5,197,467 | 3/1993 | Steinhaus et al. . |
| 5,201,808 | 4/1993 | Steinhaus et al. . |

Primary Examiner—William E. Kamm
Assistant Examiner—Scott M. Getzow
Attorney, Agent, or Firm—John R. Merkling

[57] ABSTRACT

An implantable, rate responsive pacemaker, sensitive to impedance changes in the heart as an indicator of cardiac stroke volume, wherein common interfering signals such as the intracardiac electrogram, myoelectric signals, pacing artifacts and pacing after-potentials are eliminated from the measurement of impedance. The cardiac pacemaker senses varying impedance of the heart by discharging an active capacitor through an electrode implanted within the heart to a second electrode or to the case or can of the pacemaker. The active capacitor is discharged for a selected short period of time after which the voltage remaining on the capacitor is measured. To minimize error in the measurement of voltage discharged from the active capacitor, the selected short period of time for discharge can be varied dynamically by the cardiac pacemaker. Prior to discharge of this active capacitor, however, the cardiac pacemaker samples the electrical condition of the heart or the body of the patient between the two electrodes by charging a passive capacitor. The sampled voltage on the passive capacitor is subtracted from the residual voltage on the active capacitor and the resulting voltage is used to adjust the rate of the pacemaker.

26 Claims, 4 Drawing Sheets

RATE RESPONSIVE CARDIAC PACEMAKER WITH FILTERED IMPEDANCE SENSING AND METHOD

FIELD OF MY INVENTION

My invention relates to rate responsive cardiac pacemakers, and more particularly to cardiac pacemakers which automatically adjust their pacing parameters, for example, the pacing rate in response to measured impedance, and most particularly in response to measured impedance changes in the heart.

BACKGROUND OF MY INVENTION

Implanted cardiac pacemakers are employed to assist patients suffering from severe bradycardia or chronotropic incompetence. Originally, such pacemakers restored a normal, at rest, heart rate by providing a fixed rate or narrow range of externally programmable rates. However, these pacemakers failed to meet patients' metabolic demands during exercise. Consequently, so-called "rate adaptive" or "rate responsive" pacemakers were developed. These pacemakers sense some parameter correlated to physiologic need and adjust the pacing rate of the pacemaker.

Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Among these parameters are the stroke volume of the heart and the minute volume of respiration, both parameters being inferred from impedance measurements. The stroke volume of the heart is defined as the volume of blood expelled by the ventricle in a single beat. It is equal to the difference between the end diastolic volume and the end systolic volume. In normal human subjects with healthy hearts, the stroke volume of the heart has been found to remain relatively constant over a wide range of exertion. Increases in cardiac output required to meet physiologic needs are primarily provided by increased heart rate. For certain patients with pacemakers whose heart rate is controlled by the pacemaker, increased cardiac output during exertion is provided by the heart attempting to increase its stroke volume. The stroke volume cannot increase, however, by a factor more than about two to two and a half times. Increasing the pacing rate is therefore still desired. It has been proposed to utilize the body's tendency to attempt to increase stroke volume to adjust the pacing rate of an implanted pacemaker, thereby providing an appropriate physiologic pacing rate.

For example, in Salo et al., U.S. Pat. No. 4,686,987 a stroke volume responsive, rate adjusting pacemaker is described. An AC signal is inserted through an implanted lead. The changing volume of the heart alters the impedance between the lead electrode and another electrode or the can of the pacemaker, and the changing impedance modulates the detected AC signal. By isolating the resulting amplitude envelope, an indication of the changing impedance can be obtained. This fluctuation is deemed to be a function, at least in part, of the action of the heart.

Chirife, U.S. Pat. No. 5,154,171, proposed that metabolic demands should be related to the ejection fraction, as a more accurate measure of true physiologic need. The ejection fraction is the stroke volume divided by the end diastolic volume. The stroke volume is taken to be the end diastolic volume minus the end systolic volume. The observed impedance of the heart is deemed to be a function of volume of the heart and therefore to be an indication of the desired measurements when taken at an appropriate time.

The impedance of the body, however, is not solely related to the beating of the heart. Other motions and factors also change the impedance characteristics. One example is change due to respiration. It has been proposed that the minute volume of respiration could be detected by an appropriate impedance measurement. See, for example, U.S. Pat. No. 4,901,725 entitled "Minute Volume Rate Responsive Pacemaker" to Nappholz et al.

U.S. Pat. No. 5,201,808 to Steinhaus et al., describes several attempts to detect the minute volume due to respiration in an accurate manner. Steinhaus et al. also proposes a relatively high frequency wave form as the appropriate means for measuring the spatial impedance as a function of the patient's pleural pressure. Steinhaus et al. notes that different frequencies for the testing pulse are adapted to detecting different phenomenon. That is, one range of frequency may be more appropriate for detecting changes due to heart beats, another would be more appropriate for detecting minute volume.

Of particular relevance to my invention is the apparatus described in U.S. Pat. No. 5,197,467 to Steinhaus, et al. In particular, Steinhaus, et al. describes charging a capacitor (see particularly FIG. 2) and discharging the capacitor through the heart or a portion of the body for a selected brief interval. The voltage remaining on the capacitor after the period of discharge can be detected through a buffer, converted to digital information, and used to estimate the impedance of that portion of the patient's body between the cathode and anode electrodes.

However, a problem raised by the use of impedance as an indirect measure of physiologic need is the indeterminate current path. The impedance of the body is generally measured between at least two points within the body, perhaps an electrode in the heart and a second electrode the can of an implanted device. The path between these to points, however, is inherently indeterminate. Moreover, the measurement may be affected by motion of the electrode tip, by conditions surrounding the tip or by electrical capacitances adjacent electrodes (as described in Steinhaus et al. '808), or other factors. In general, however, these factors are relatively slow to change, as compared to changes in impedance due to the beating of the heart. Moreover, I have observed that changes in impedance due to heart beats are usually on the order of 0.5 to 20 ohms whereas long-term changes, representing a baseline impedance, have a magnitude of about 500 ohms and tend to vary over a range of several hundred ohms. In addition, since the impedance is measured indirectly by measuring a voltage and deriving the impedance, the intrinsic electrical condition of the heart can distort the measurement of impedance. Myopotentials, pacing artifacts, pacing after potentials, and general electrical noise can all mask the desired measurement. It is desirable, therefore, to eliminate or minimize the effect of background interference or apparent baseline impedance so that changes in impedance due to the relatively fast beating heart or to respiration may be amplified and more easily detected.

SUMMARY OF MY INVENTION

I have invented an implantable, rate responsive pacemaker, sensitive to impedance changes in the heart as an indicator of cardiac stroke volume, wherein common interfering signals such as the intracardiac electrogram, myoelectric signals, pacing artifacts and pacing after-potentials are eliminated from the measurement of impedance. This enhances the pacemaker ability to distinguish cardiac-related changes in impedance.

In the preferred embodiment of my invention, a cardiac pacemaker senses varying impedance of the heart by discharging an active capacitor through an electrode implanted within the heart to a second electrode or to the case or can of the pacemaker. The active capacitor is discharged for a selected short period of time after which the voltage remaining on the capacitor is buffered for further processing. Prior to discharge of this active capacitor, however, the cardiac pacemaker of my invention samples the electrical condition of the heart or the body of the patient between the two electrodes by charging a passive capacitor. The voltage on this passive capacitor is also buffered and held in a sample and hold circuit until the active capacitor has been discharged. The voltage on the passive capacitor is subtracted from the residual voltage on the active capacitor and the resulting voltage is held in a sample and hold circuit. The voltage held in the sample and hold circuit is communicated to a microprocessor for adjustment of the rate of the pacemaker. To minimize error in the measurement of voltage discharged from the active capacitor, the selected short period of time for discharge can be varied dynamically by the cardiac pacemaker.

It is the principal object of my invention, therefore, to provide a rate-responsive pacemaker which can more accurately detect impedance changes in the heart.

A further object of my invention is to provide an impedance sensitive pacemaker which can reject background and interference signals such as the intracardiac electrogram, myoelectric signals, pacing potential artifacts, and pacing after-potentials, for example.

Another object of my invention is to provide a rate responsive pacemaker which can amplify the effects of cardiac related impedance changes.

Another important object of my invention is to provide a rate responsive pacer which is more selectively responsive to cardiac stoke volume changes, as indicated by changes in cardiac impedance.

A further object of my invention is to provide a rate responsive, impedance sensing pacemaker which varies a discharge time of an active capacitor to reduce error in measurement of discharge voltages.

These and other objects and features of my invention will be apparent to the skilled artisan from the following detailed description taken with reference to the accompanying drawings.

DETAILED DESCRIPTION OF MY PREFERRED EMBODIMENT

I will now describe the preferred embodiment of my invention with reference to the accompanying figures. Like numerals will be used to designate like parts throughout.

Figure 1:
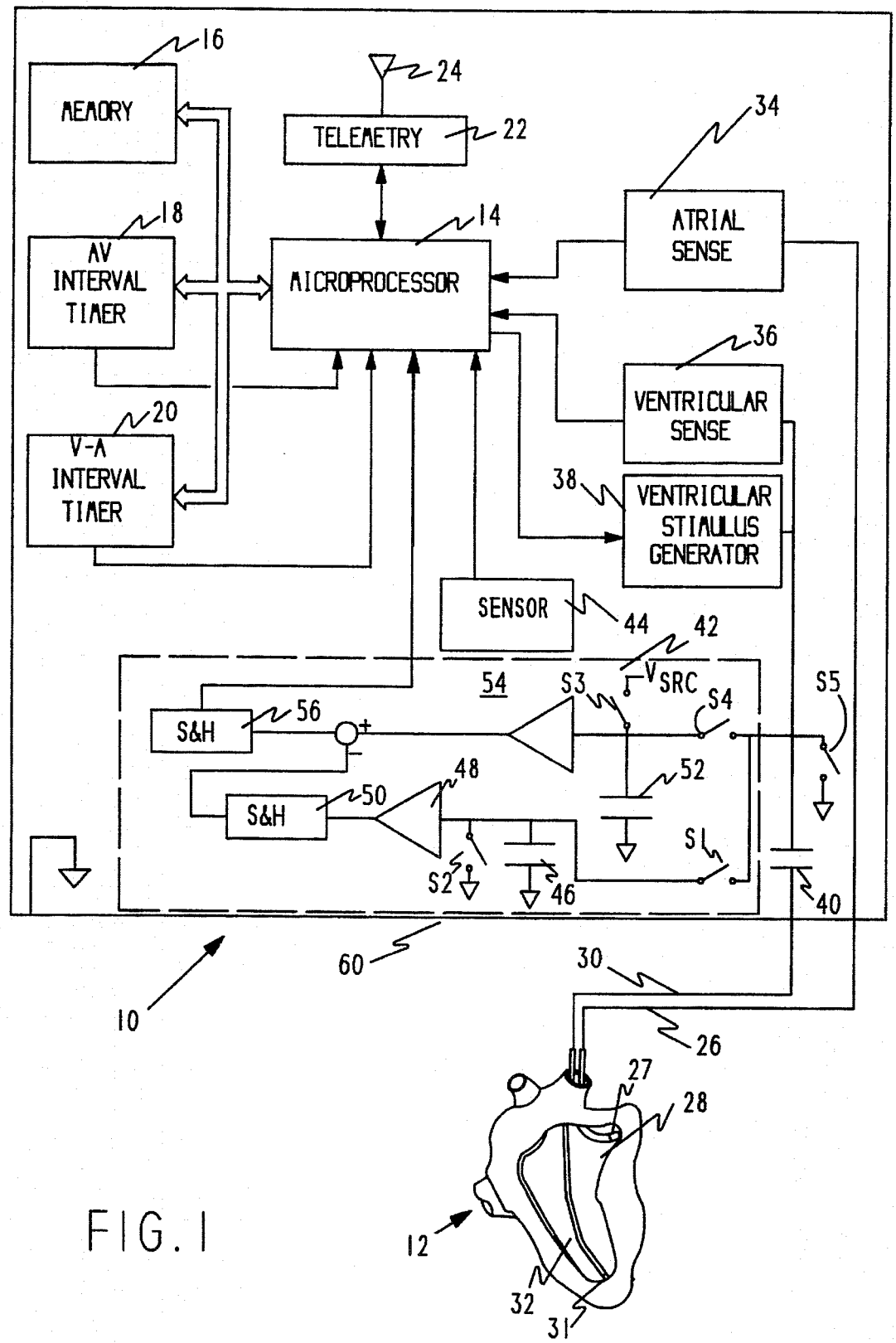
FIG. 1 is a block diagram of a first preferred embodiment of a rate adaptive pacemaker according to my invention.

Referring now to FIG. 1, a pacemaker, generally designated 10, is illustrated in schematic fashion with connection to a human heart 12. For ease of illustration, I have elected to describe my invention in connection with a pacemaker having atrial sensing and ventricular sensing and pacing. It should be understood, however, that my invention can be employed for sensing in the atrium, the ventricle or both and that both atrial or ventricular pacing could be provided without departing from the teachings of my invention. In addition, the features of my invention could also be combined with an implantable defibrillator/cardiovertor.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 so that communication can be had across an antenna 24 to an external programmer (not shown). Telemetry permits an attending physician to obtain data and information from the pacemaker and to control the pacemaker to set various selectable parameters, as known in the art.

The pacemaker 10 is connected to the heart 12 through a first lead 26 to an electrode 27 in the atrium 28 and through a second lead 30 to an electrode 31 in the ventricle 32. An indifferent electrode is provided to complete the electrical circuit. In the illustrated embodiment, a can 60 or outer casing of the pacemaker serves as the indifferent electrode. Bipolar leads can also be used with my invention as well as the unipolar leads illustrated here. Atrial sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the scope of those skilled in the art to provide atrial pacing, should that be desired, or to provide cardioversion/defibrillation capabilities in response to the detected condition of the heart. Stimulation of the heart is passed through a coupling capacitor 40 in a conventional fashion. A switch S5, connected to ground, is periodically closed to discharge the capacitor 40 and balance stimulation pulses, producing a net zero charge at the electrode.

To control the pulse rate of the ventricular stimulus generator 38, the microprocessor acquires information on the condition of the heart through an impedance circuit 42. The impedance circuit 42 detects changes in impedance primarily due to the changing shape of the heart, which is related to the physical shape of the heart as it beats and pumps blood. This information can be used to derive a measure of the stroke volume or ejection fraction of the heart.

In addition to the measurement of impedance, a sensor 44 may also be provided to obtain an indication of physiologic need and adjust the pacing rate. Such a sensor may be an accelerometer, as described by Dahl, U.S. Pat. No. 4,140,132, (incorporated herein by reference) a temperature sensor, as described by Alt, U.S. Pat. No. 4,688,573 (also incorporated herein by reference), or any other suitable sensor of a parameter which may be correlated to physiologic need of the patient.

The impedance circuit 42 comprises a first capacitor 46 which I will call a passive capacitor. This capacitor is connected to the lead 30 through a switch S1 and to ground through a second switch S2. The capacitor is also connected to a buffer 48 in common with the two switches S1 and S2. On the other side of the capacitor 46, the capacitor 46 is connected to ground. The buffer 48 communicates with a sample and hold circuit 50. The function of the separate sample and hold circuit 50 can be performed by the passive capacitor 46 and the buffer 48, if the sampling time (see FIG. 5) is short and the impedance of the buffer 48 is high. Each of the two switches S1 and S2 and the sample and hold circuit 50 are controlled by the microprocessor 14. Such connections are well known in the art and are not illustrated for the sake of clarity. A second capacitor 52, which I will call an active capacitor, is also connected to the lead 30 through a switch S4. Preferably, the passive capacitor is of similar magnitude to the active capacitor, and most preferably the passive capacitor has the same capacitance as the active capacitor. This enables the passive capacitor to serve as an accurate model of the effect of background voltages on the active capacitor, as will be more fully explained below.

The side of the active capacitor 52 connected to the lead is further connected through a switch S3 to a voltage source, labeled $V_{SRC}$ in FIG. 1. Finally, the capacitor is connected in common with the two switches S4 and S3 to a buffer 54. The other side of the capacitor 52 is connected to ground. The output of the buffer 54 is combined with the output of the sample and hold circuit 50, as will be more particularly described below, by subtracting the voltage of the sample and hold circuit 50 from the output of the buffer 54. The resulting voltage is held in a second sample and hold circuit 56 until required by the microprocessor. Typically, the analog value of the voltage held by the sample and hold circuit 56 is converted to a digital value for further processing. As explained above, the switches S3 and S4 and the sample and hold circuit 56 are controlled by the microprocessor 14 in a manner similar to that of switches S1 and S2 and sample and hold circuit 50.

Figure 5:
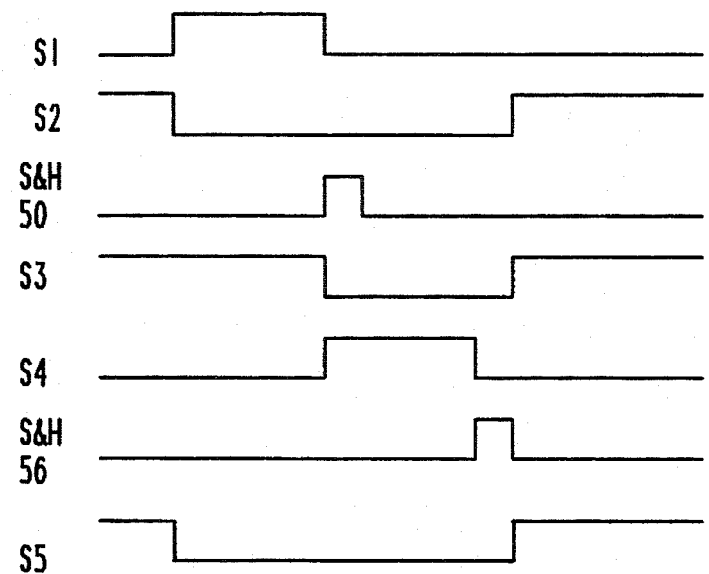
FIG. 5 is a timing diagram.

The operation of the impedance circuit 42 can be understood with respect to a timing diagram, FIG. 5. Preferably, the impedance circuit determines the impedance of the heart at a relatively high rate, on the order of 100 times per second. A single operational cycle is described with respect to FIG. 5. As each cycle begins, passive capacitor 46 is in a discharged state while active capacitor 52 is charged to a preselected voltage level, $V_{SRC}$, which may be about 0.5 V or less. Initially, during the cycle, S1 is closed for a preselected period, for example, 15 μsec. This is indicated in the timing diagram of FIG. 5 by the line S1 going high. Simultaneously, switch S2 is opened as indicated by the line S2 going low. This effectively connects the passive capacitor 46 through the lead 30 to the electrode 31 within the heart 12. The passive capacitor 46 assumes the electrical value of the electrode 31 during the time that switch S1 is closed.

After switch S1 opens, the electrical condition of the passive capacitor 46 appears through the buffer 48 at the sample and hold circuit 50. The sample and hold circuit 50 is therefore triggered by the microprocessor to capture this voltage as indicated by the line S/H 50 going high. While the passive capacitor 46 is charged from the electrical condition of the head, the active capacitor 52 is charged from $V_{SRC}$ through S3 as indicated by the high condition of line S3 in FIG. 5. When switch S1 opens, switch S3 also opens as indicated by the low condition of line S3. Simultaneously, switch S4 closes, as shown by line S4 in FIG. 5, for a preselected period of time, for example 15 μsec. If the active capacitor 52 has the same capacitance as the passive capacitor 46, as described above, and if the resistance of the two switches S4 and S1 are equal, then S1 is preferably activated for the same length of time as S4. The active capacitor 52 discharges through switch S4 and lead 30 through the electrode 31 in the head. Electrical current passes from the electrode 31 within the head to an anode on lead 30 or to the can 60 of the pacemaker which acts as an indifferent electrode.

When S4 opens, S3 does not immediately close. Rather, the electrical condition of the active capacitor 52 is passed through buffer 54. The electrical value retained in the sample and hold circuit 50, representing the electrical condition of the head, is subtracted from the output of buffer 54 and the resulting value is captured by the sample and hold circuit 56, as represented by line S/H 56 going high. After the sampling by sample and hold circuit 56 is complete, initial conditions on the capacitors 46, 52 can be restored by connecting the passive capacitor 46 to ground through S2 (indicated by line S2 going high) and the active capacitor 52 to $V_{SRC}$ through switch S3 (indicated by line S3 going high). In addition, pacing and impedance sensor pulses are usually passed to the head through an AC-coupling capacitor 40. Switch 55 is used to discharge this capacitor and to produce a balanced pulse which results in zero net charge flow through the tissue. This is indicated by line S5 going high, closing switch S5. Switch S5 opens when line S5 goes low.

S4 being closed (see FIG. 5) represents a selected short period of time during which the active capacitor 52 is discharged through the heart. The voltage on the active capacitor 52 decays exponentially according to the following formula:

$$V_{CA}(t) = V_0 e^{-t/RCa}$$

Where $V_{CA}$ is the voltage remaining on the active capacitor after a time t; $V_0$ is the initial voltage on the capacitor; R is the lumped resistance of the circuit, and Ca is the capacitance of the active capacitor 52. There is an error associated with making the measurement of $V_{CA}$ as there is in making any measurement. This error can be minimized, however, by making the measurement after an elapsed time T equal to one time constant that is, at t=T=RCa. The desired measured value is R determined as follows:

$$R = -t/(Ca\ ln(V_{CA}(t)/V_0))$$

The fractional error in the measurement of R, that is, d(ln R), is a function which has a minimum at t=T=RCa. The function is:

$$d(ln\ R) = -[ln(V_{CA}(t)/V_0)]^{-1}[V_{CA}(t)/V_0]^{-1}$$

Figure 6:
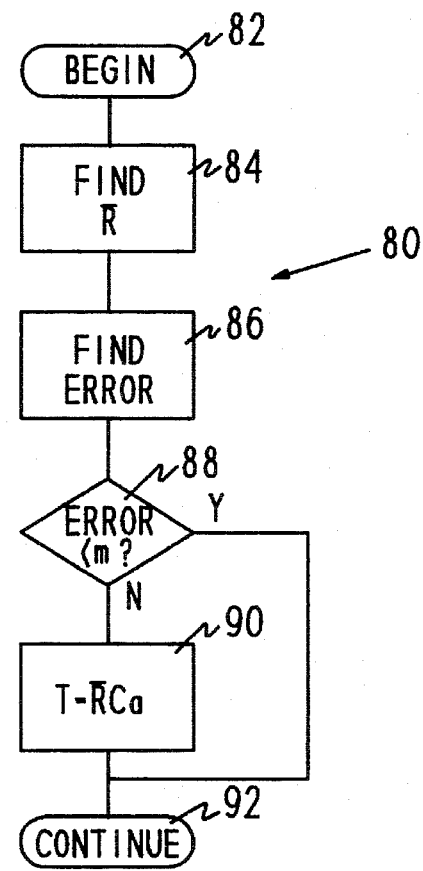
FIG. 6 is a flow chart of an algorithm for minimizing error in voltage measurement on an active capacitor.

The value Ca, the capacitance of the active capacitor, is constant, but the value R, the impedance of the circuit including the heart, is changing. The error associated with the measurement of $V_{CA}$ (and thus also the error associated with the impedance) can be minimized by programming the microcomputer 14 to dynamically adjust the time during which S4 is open. A suitable procedure, generally designated 80, is illustrated diagrammatically in FIG. 6.

The procedure 80 is part of the general operation of the microcomputer 14. When the procedure 80 begins 82, an average or representative value of the impedance R̄ is determined 84. This could, for example be the rolling average of the measured value of the impedance for a predetermined number of cycles. The fractional error d(ln R) is then computed 86. The fractional error is compared 88 to an acceptable value m. If the fractional error is less that the acceptable value m, the value t, that is the time switch S4 is open, is unchanged. If the fractional error is greater than the acceptable value m, a new value of t is calculated 90 such that $t=\bar{R}$ Ca. The microprocessor proceeds 92 with other processing, using the new value t to determine the impedance from the measured value of $V_{CA}$ after a discharge time t.

Figure 2:
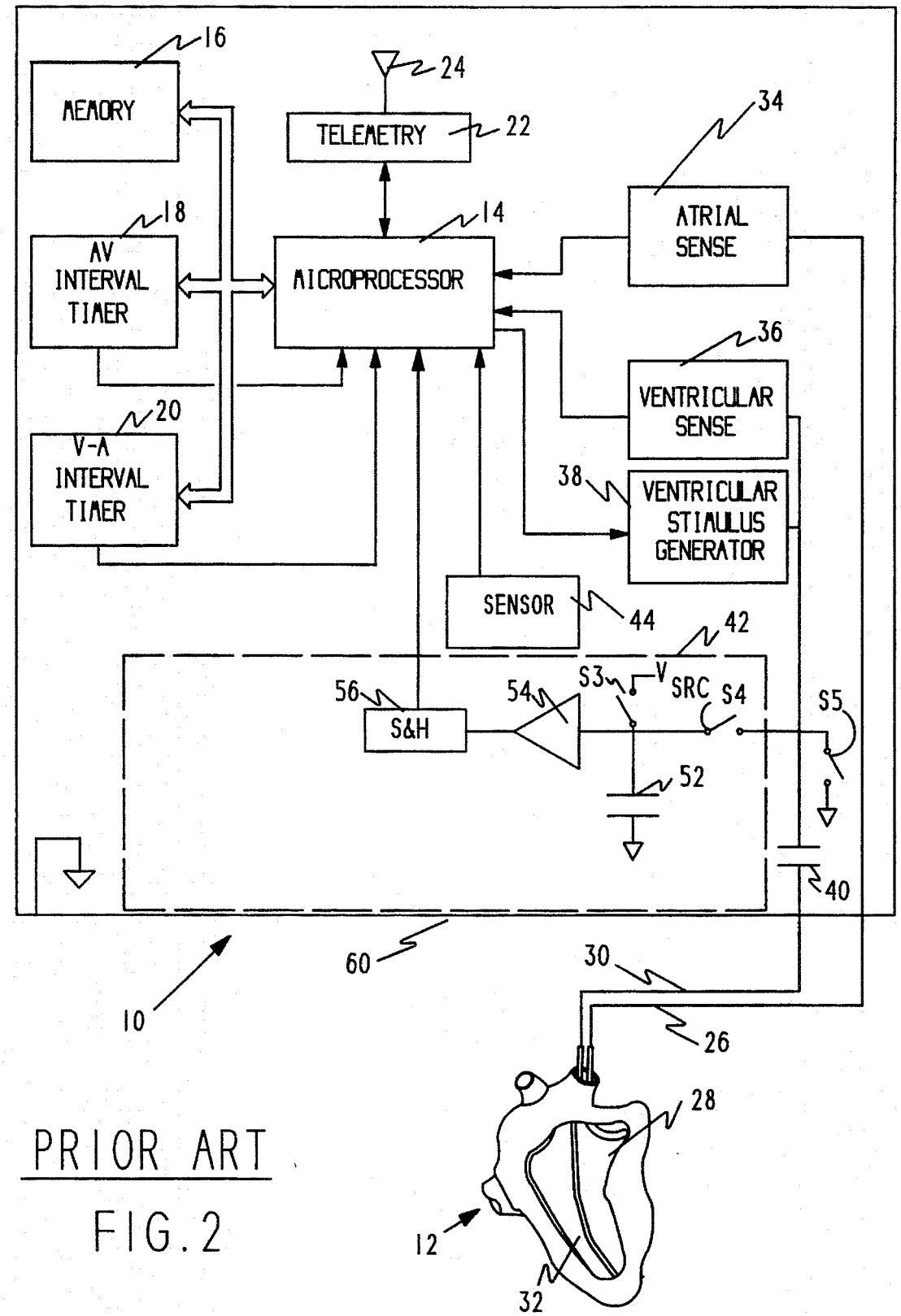
FIG. 2 is a block diagram of a prior art rate adaptive pacemaker.
Figure 3:
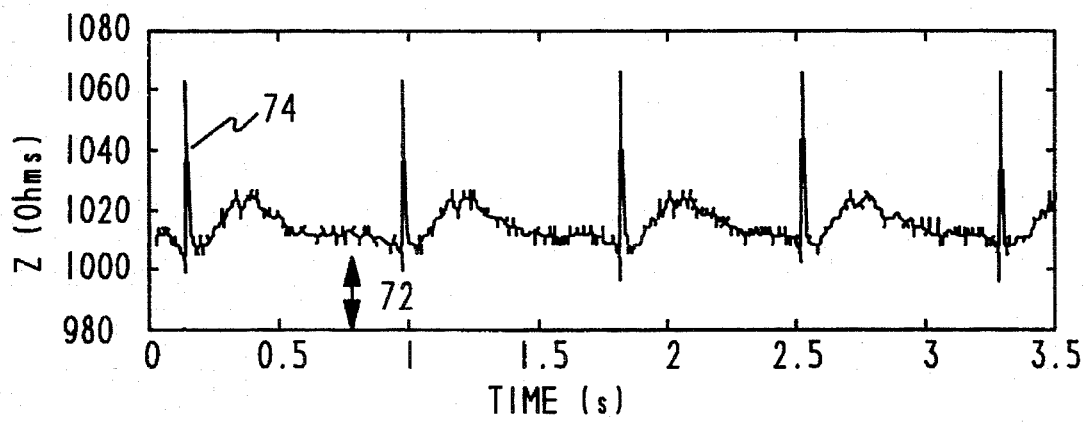
FIG. 3 is a graph of voltage as a measure of impedance as detected by the prior-art pacemaker of FIG. 2.

Prior art devices, such as that described by Steinhaus, et al. in U.S. Pat. No. 5,197,467, did not provide the sampling circuitry for detecting the inherent electrical condition of the heart as described herein. In FIG. 2, I have illustrated a prior art device, such as described by Steinhaus, et al. (The disclosure of U.S. Pat. No. 5,197,467 is incorporated herein by reference.) All the components are labeled as in connection with FIG. 1. It can be seen that only the active capacitor 52 with its associated switches S3 and S4, buffer 54 and sample and hold circuit 56 have been provided. With the prior art circuit 52, the electrical condition of the heart tends to mask or obscure the desired impedance measurement resulting from the changing physical configuration of the heart. This is illustrated in FIG. 3. FIG. 3 represents an impedance 70 corresponding to measurements which would be obtained through the sample and hold circuit 56 in the prior art device of FIG. 2. Because the electrical polarization potentials, pacing after potentials, and other components along the current path would also be sensed, a large offset or baseline value 72 could be detected. In addition, intracardiac electrogram artifacts, for example artifact 74, would also be detected. The signal could also be distorted by myopotentials and other artifacts not related to the impedance.

Figure 4:
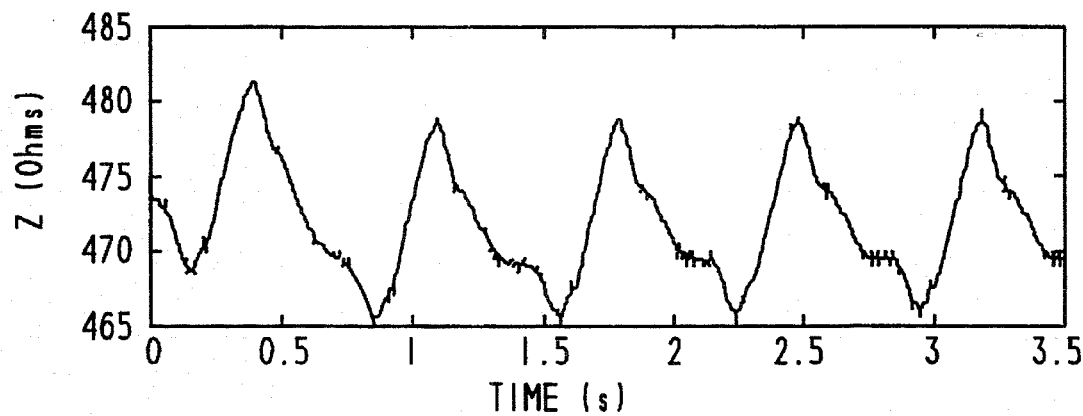
FIG. 4 is a graph of voltage as a measure of impedance as detected by a pacemaker according to my invention.

FIG. 4, on the other hand, illustrates measurement of impedance using an impedance circuit in accordance with my invention. Offset due to artifacts and background electrical condition is eliminated, as are the effects arising from myopotentials, cardiac pacing, and pacing after-potentials. The resulting signal more nearly represents actual changes in impedance related to the physical action of the heart.

Having identified impedance information associated with cardiac contractions, this information can then be used to control the pacing rate or other pacing parameters, such as A-V delay intervals. By controlling the pacing rate in such a manner as to keep the stroke volume relatively constant from cycle to cycle, a physiologically appropriate pacing rate is selected.

My invention may be embodied in other specific forms without departing from the spirit or essential characteristics thereof. The foregoing description is, therefore, to be viewed in all respects as illustrative and not restrictive. The scope of my invention is defined by the appended claims.

I claim as my invention:

1. A cardiac stimulation apparatus comprising means for pacing a patient's heart;

means for measuring impedance within the patient's body, said impedance measuring means including means for sampling an intrinsic voltage condition of the patient's body at at least one location within the patient's body and for producing a first signal correlated to said intrinsic voltage condition, means for applying an electric current between at least two points on said apparatus, means for sensing a voltage in response to the application of said electrical current and for producing a second signal correlated to said voltage, and means for combining said first and second signals to produce a combined signal;

means for deriving a metabolic demand parameter from said combined signal; and means for adjusting a pacing parameter in relation to said metabolic demand parameter.

2. The cardiac stimulation apparatus according to claim 1 wherein said means for measuring impedance further comprises timing means for controlling said means for sampling to sample said intrinsic voltage condition during a first pre-determined time and for controlling said means for applying said electric current to apply said electric current during a second pre-determined period of time.

3. The cardiac stimulation apparatus according to claim 2 wherein said means for combining said first and second signals comprises means for subtracting said second signal from said first signal.

4. The cardiac stimulation apparatus according to claim 3 further comprising means for sensing a second parameter correlated to physiologic need of said patient and wherein said means for determining said pacing parameter in relation to said metabolic demand parameter further comprises means for determining said pacing parameter in relation to both said demand parameter and said second parameter.

5. The cardiac stimulation apparatus according to claim 1 wherein said means for combining said first and second signals comprises means for subtracting said second signal from said first signal.

6. The cardiac stimulation apparatus according to claim 5 further comprising means for sensing a second parameter correlated to physiologic need of said patient and wherein said means for determining said pacing parameter in relation to said metabolic demand parameter further comprises means for determining said pacing parameter in relation to both said demand parameter and said second parameter.

7. The cardiac stimulation apparatus according to claim 1 further comprising means for sensing a second parameter correlated to physiologic need of said patient and wherein said means for determining said pacing parameter in relation to said metabolic demand parameter further comprises means for determining said pacing parameter in relation to both said demand parameter and said second parameter.

8. The cardiac stimulation apparatus according to claim 1 wherein said means for sampling comprises a passive capacitor.

9. The cardiac stimulation apparatus according to claim 8 wherein said means for sampling further comprises a buffer and a sample and hold circuit.

10. The cardiac stimulation apparatus according to claim 9 wherein said means for measuring impedance further comprises timing means for controlling said means for sampling to sample said intrinsic voltage condition during a first pre-determined time and for controlling said means for applying said electric current to apply said electric current during a second pre-determined period of time.

11. The cardiac stimulation apparatus according to claim 10 wherein said means for combining said first and second signals comprises means for subtracting said second signal from said first signal.

12. The cardiac stimulation apparatus according to claim 11 wherein said means for combining said first and second signals further comprises a sample and hold circuit.

13. The cardiac stimulation apparatus according to claim 12 further comprising means for sensing a second parameter correlated to physiologic need of said patient and wherein said means for determining said pacing parameter in relation to said metabolic demand parameter further comprises means for determining said pacing parameter in relation to both said demand parameter and said second parameter.

14. The cardiac stimulation apparatus according to claim 1 wherein said means for applying an electric current further comprises means for variably controlling a length of time during which said electric current is applied and wherein said means for sensing a voltage in response to the application of said electric current is responsive to sample said voltage at the end of said length of time and wherein said cardiac stimulation apparatus further comprises means for dynamically adjusting said length of time.

15. The cardiac stimulation apparatus according to claim 14 wherein said means for applying an electric current comprises an active capacitance and said means for dynamically adjusting said length of time comprises means for setting said length of time as a function of said active capacitance and said metabolic demand parameter.

16. The cardiac stimulation apparatus according to claim 15 wherein said means for setting said length of time comprise means for setting said length of time to a length of time substantially equal to a product of said active capacitance and a rolling average of said metabolic demand parameter.

17. A method for controlling a cardiac stimulation apparatus for pacing a patient's heart at a controlled rate comprising the steps of:

sampling an intrinsic voltage condition of the patient's body at at least one location within the patient's body, producing a first signal correlated to said intrinsic voltage condition, applying an electric current between at least two points on said apparatus, sensing a voltage in response to the application of said electrical current producing a second signal correlated to said voltage, combining said first and second signals to produce a combined signal;

deriving a metabolic demand parameter from said combined signal; and determining said controlled rate in relation to said metabolic demand parameter.

18. The method according to claim 17 further comprising timing said step of sampling to sample said intrinsic voltage condition during a first pre-determined time, and timing said step of applying said electric current to apply said electric current during a second pre-determined period of time.

19. The method according to claim 18 wherein said step of combining said first and second signals comprises subtracting said second signal from said first signal.

20. The method according to claim 19 further comprising sensing a second parameter correlated to physiologic need of said patient and wherein said step of determining said controlled rate in relation to said metabolic demand parameter further comprises determining said controlled rate in relation to both said parameters.

21. The method according to claim 17 wherein said step of combining said first and second signals comprises subtracting said second signal from said first signal.

22. The method according to claim 21 further comprising sensing a second parameter correlated to physiologic need of said patient and wherein said step of determining said controlled rate in relation to said metabolic demand parameter further comprises determining said controlled rate in relation to both said parameters.

23. The method according to claim 17 further comprising sensing a second parameter correlated to physiologic need of said patient and wherein said step of determining said controlled rate in relation to said metabolic demand parameter further comprises determining said controlled rate in relation to both said parameters.

24. A cardiac stimulation apparatus comprising means for pacing a patient's heart;

means for measuring impedance within the patient's body, said impedance measuring means including means for applying an electric current between at least two points on said apparatus, said means for applying an electric current further having means for variably controlling a length of time during which said electric current is applied, means for periodically and automatically adjusting said length of time to minimize measuring error, and means for sensing a voltage in response to the application of said electrical current responsive to sample said voltage at the end of said length of time and for producing a signal correlated to said voltage, means for deriving a metabolic demand parameter from said signal; and means for adjusting a pacing parameter in relation to said metabolic demand parameter.

25. The cardiac stimulation apparatus according to claim 24 wherein said means for applying an electric current comprises an active capacitance and said means for dynamically adjusting said length of time comprises means for setting said length of time as a function of said active capacitance and said metabolic demand parameter.

26. The cardiac stimulation apparatus according to claim 25 wherein said means for setting said length of time comprise means for setting said length of time to a length of time substantially equal to a product of said active capacitance and a rolling average of said metabolic demand parameter.

* * * * *